United States Patent [19]

Bustance et al.

[11] Patent Number: 4,632,132
[45] Date of Patent: Dec. 30, 1986

[54] TREATED END WRAP LAMINATE

[75] Inventors: William G. Bustance; Robert E. Borey, both of Traverse City, Mich.

[73] Assignee: Totally, Inc., Traverse City, Mich.

[21] Appl. No.: 459,055

[22] Filed: Jan. 19, 1983

[51] Int. Cl.[4] .............................................. A45D 7/00
[52] U.S. Cl. ............................................ 132/7; 132/9
[58] Field of Search ................ 132/7, 43 A; 128/355, 128/156, 62 R; 117/67

[56] References Cited

U.S. PATENT DOCUMENTS

| | | | |
|---|---|---|---|
| 1,748,008 | 2/1930 | Barnowitz | 128/62 R |
| 1,994,099 | 3/1935 | Fulton | 132/43 A |
| 2,118,101 | 5/1938 | Nollau et al. | 128/156 X |
| 2,241,384 | 5/1941 | Bateman et al. | 128/156 X |
| 2,529,886 | 11/1950 | Semco | 132/7 |
| 2,906,273 | 9/1959 | Beauregard | 132/7 |
| 2,991,790 | 7/1961 | Bonilla | 132/7 |
| 3,345,993 | 10/1967 | Haefele | 132/7 |
| 3,367,345 | 2/1968 | Riley | 132/7 |
| 3,465,759 | 9/1969 | Haefele | 132/7 |
| 3,470,877 | 10/1969 | Morgan | 128/355 |
| 3,955,586 | 5/1976 | Hartsough | 132/7 |
| 4,112,177 | 9/1978 | Salditt | 128/156 |
| 4,130,121 | 12/1978 | Wetzel | 132/7 |
| 4,403,622 | 9/1983 | Stahl | 132/7 |

*Primary Examiner*—Gregory E. McNeill
*Attorney, Agent, or Firm*—John A. Waters

[57] ABSTRACT

A treated end wrap laminate for use in permanent hair waving including an exterior sheet of impermeable flexible plastic, an interior sheet of absorbent flexible paper impregnated with a hair waving solution counteractant and a middle layer of adhesive uniformly bonding the sheets together. The unique end wrap protects the hair from unwanted exposure to hair waving solution and counteracts the solution during the permanent hair waving process.

19 Claims, No Drawings

TREATED END WRAP LAMINATE

BACKGROUND OF THE INVENTION

1. Field of the Invention

The present invention relates to end wraps, and, more particularly to a treated end wrap laminate for use in permanent hair waving.

2. Description of the Prior Art

Permanent hair waving has been in widespread use for many years. In recent years, cold waving has become increasingly popular because of its ease and convenience, which permits consumers the option of waving their own hair without professional assistance. In cold waving, tresses of hair are wound on individual rods or rollers, and a waving solution is applied to the hair which contains a reducing agent to break the disulfide linkages present in the keratin of the hair. The broken disulfide linkages are then permitted to realign themselves while the hair is rolled on the rollers. The hair is then rinsed and neutralized by chemical or air oxidation which rebonds the hair in the new configuration by reforming disulfide linkages.

To facilitate rolling of the tresses of hair on the individual rollers, small rectangular pieces of paper or other similar material known as end wraps are folded and placed around the free ends of the hair tresses just prior to rolling. Although ordinary end wraps function satisfactorily to facilitate rolling of the hair tresses, they tend to collect and concentrate the waving solution, thus over-exposing the ends of the hair tresses. This generally results in undue frizziness, curling, harshness and dryness of the hair ends. Because of this problem, a wide variety of end wraps have been developed to protect the wrapped hair ends from over-exposure to the hair waving solution. For example, ordinary end papers have been impregnated with chemicals which function to neutralize the reducing agent of the waving solution. Other developments rely on physically blocking access of the reducing agent to the hair ends by constructing the end papers from special impervious foamed plastics. A recent innovation utilizes an open celled polyether polyurethane foam which contains a chemical buffer system to neutralize the waving solution reducing agent.

While some of these modified end wraps provide a certain degree of protection for the hair ends, they have not proven to provide reliable and complete protection. In the case of the special foamed plastic end wraps which rely on providing a physical barrier, some leakage can and does occur, especially when the hair is rolled by a novice. The end wraps which rely solely on chemical neutralizers or buffering systems for protection also tend to fail if the application of the waving solution is too generous.

Another problem with the current modified end wraps is cost. Since end papers are not reusable, the use of expensive specialized foamed plastics or complex chemical neutralizers yields a significant increase in the cost of each permanent. In addition, the cost of the protective type of end papers is becoming even more significant in affecting the overall cost of the permanent because of recent changes in hair fashions. For example, the popularity of hair styles with curl in the body of the hair with loose, uncurled ends has led to increasing numbers of "root perms" where the protective end papers are utilized in greater quantities and of various lengths and widths to produce the desired hair style, as opposed to merely protecting the hair ends from damage.

Thus, there is a current need for a protective end paper which not only provides complete and reliable protection but which is also inexpensive and easy to use.

SUMMARY OF THE INVENTION

According to the present invention, there is provided a treated end wrap laminate for use in permanent hair waving which reliably and completely protects the wrapped hair from the reducing agent of hair waving solutions. The unique end wrap laminate is inexpensive and easy to use.

The end wrap laminate includes an exterior sheet of impermeable flexible plastic, preferably texturized polyethylene with a thickness of from about 0.2 to about 1.0 mils, and an interior sheet of absorbent flexible paper impregnated with a hair waving solution counteractant. The paper is preferably a wet-strength tissue paper having a density of from about 8 to about 10 pounds per cubic foot and has a thickness of from about 1 to about 2 mils. The exterior sheet and the interior sheet, which have the same configuration, are uniformly bonded together by a middle layer of adhesive.

The preferred hair waving solution counteractant is calcium chloride, which is preferably applied to the end wrap paper as a substantially saturated aqueous solution, followed by evaporating substantially all of the water. It is especially preferred to also impregnate the end wrap paper with at least one hair conditioner.

Rectangular configurations for the end wrap laminates are preferred.

DESCRIPTION OF THE PREFERRED EMBODIMENT

The end wrap laminates of the present invention are unique in that they provide a dual protection system, including both physical and chemical protection. The exterior sheet provides the physical barrier to the waving solution and thus must be impermeable. In addition, it must be flexible and tear-resistent in thin sheets to facilitate rolling and handling with ease and without fear of punctures or tears. While a variety of materials can be used, such as polyvinyl chloride, polyvinyl alcohol, "Mylar", cellophane, rubber, cellulose acetate or the like, the preferred plastic material is polyethylene. This is because of its low cost, reliability, flexibility and tear-resistance in very thin sheets. Especially preferred is texturized polyethylene which increases tear-resistance in thin sheets, as well as optimizing the physical barrier of the end wrap by minimizing seepage of the waving solution between adjacent wrapped layers of the end wrap.

It has also been found that the thinner the plastic, the easier the rolling operation, especially when using small rollers or short hair tresses. In addition, the thinner plastic yields a more impervious roll because it rolls more uniformly. It has been found that a plastic thickness of from about 0.2 to about 1.0 mils optimizes the handling and sealing characteristics with sufficient tear-resistance.

The primary function of the interior paper sheet is to provide a carrier for the hair waving solution counteractant. Thus, absorbency is important. In addition, however, it also must be flexible to facilitate handling and rolling of the end wrap. While the primary tear-resistance of the end wrap is provided by the exterior plastic sheet, the paper must have sufficient wet strength when saturated to maintain its integrity. While a variety of paper materials may be utilized, such as porous filter paper or various composites of rag and wood fibers, the preferred paper is a wet strength tissue with a density of from about 8 to about 10 pounds per cubic foot, which optimizes the absorbency, flexibility and strength requirements. The paper must be thin enough to facilitate handling and rolling, yet thick enough to retain sufficient hair waving solution counteractant to provide the necessary chemical protection. It has been found that the optimum thickness of the paper is from about 1 to about 2 mils.

The exterior sheet of plastic and the interior sheet of paper are uniformly bonded together by a middle layer of adhesive. The particular adhesive utilized is a matter of choice from the many adhesives commercially available. The guidelines for selecting a satisfactory adhesive are that it must yield uniform bonding in thin layers between paper and plastic, it must be water resistant and non-reactive with the hair waving solution, the counteractant or any other constituents employed during the hair waving procedure. Preferably, the adhesive should also be non-toxic. Satisfactory results have been experienced with a conventional commercially available non-toxic white glue such as "Borden's Glue All" and with industrial grade aerosol adhesives such as "Spray Adhesive 90", which is commercially available from the Adhesives, Coatings and Sealers Division of 3M, 3M Center, St. Paul, Mn. The glue may be applied by brushing, spraying or the like, as long as a thin uniform coat results.

Preferably, the plastic sheet is placed on a flat surface area and the adhesive is applied to the plastic. The paper sheet is then placed on the adhesive coated plastic sheet. The adhesive must be allowed to thoroughly dry prior to impregnating the paper with the hair waving solution counteractant. While individual end paper laminates can be assembled by bonding pre-cut and matched sheets of plastic and paper, it is preferred to bond large sheets of plastic and paper, followed by impregnating the paper, with cutting to the desired sizes of end wraps being the final step.

Once the bonding of the plastic and paper sheets is complete and dry, the paper sheet is uniformly impregnated with the hair waving solution counteractant. The counteractant must neutralize the reducing agent of the waving solution, must possess good physical retention upon impregnating the paper sheet and must not adversely react with the end wrap components or other constituents utilized in the permanent hair waving process. The vast majority of current hair waving solutions contain as the active ingredient or reducing agent thioglycolic acid or the ammonium or sodium salts thereof, with ammonium thioglycolate being the most common. Suprisingly, it has been discovered that the ideal counteractant for these thioglycolic compounds is calcium chloride, and thus calcium chloride is the preferred hair waving solution counteractant of the present invention. Unlike complex and expensive neutralizers employed heretofore, calcium chloride is inexpensive and readily available. Because of its very high solubility in water, impregnating the entire paper sheet with an aqueous solution is easily accomplished, with excellent retention properties in the paper upon evaporation of the water. In addition, upon completion of the permanent hair waving process, complete removal of the calcium chloride from the hair is insured upon a simple water rinse.

To impregnate the interior sheet of absorbent paper, an aqueous solution of calcium chloride is prepared. Since the neutralizing capacity of the end wrap laminate is directly proportional to the amount of calcium chloride impregnated, a saturated calcium chloride solution is optimum. However, concentrations as low as one part of calcium chloride to twenty parts of water, by weight, is functional, and concentrations on the order of about 8 parts of calcium chloride to about 5 parts of water, by weight, produces consistently effective results. The interior sheet of paper is impregnated by uniformly saturating it with the aqueous calcium chloride solution, e.g., by brushing, spraying or the like. The end wrap is then allowed to dry until substantially all of the water has evaporated. This can be accomplished in air at room temperature or heat or hot air can be applied to accelerate the evaporation of the water.

Once the impregnation of the end wrap is completed and dry, the desired sizes and configurations of end wraps are cut from the laminate. The most effective configuration is rectangular (including square), with dimensions ranging from about 1 inch by 1 inch to about 5 inches by 5 inches. About 2 inches by 3 inches is the preferred size for most purposes.

Since calcium chloride is a deliquescent compound, it may produce some unwanted drying of the wrapped hair in some cases. To counteract this potential side effect of calcium chloride, the paper sheet can optionally be also impregnated with one or more hair conditioners. Most of the commonly available hair conditioners, including mixtures thereof, may be used with satisfactory results, as long as they are either water soluble or water miscible and do not adversely react with the other components or constituents utilized in the hair waving operation. Surface active, non-ionic conditioners are preferred because they function not only as moisturizers, but also as dispersing agents and thus act as a carrier for the counteractant to ensure penetration of the hair tresses. This improves protection of hair not directly touching the end wrap paper. Examples of suitable conditioners are lanolin, animal protein, Ceteareth-5, which is an emollient and emulsifier produced by condensing cetyl alcohol with ethylene oxide, Choleth-24, which is an emulsifier derived from cholesterol and ethylene oxide, and Oleth-20, which is a conditioner and emulsifier derived from natural fatty alcohol, oleyl alcohol being reacted with ethylene oxide. The preferred conditioner is lanolin, with PEG-75 lanolin being especially preferred. PEG-75 lanolin is an emollient and emulsifier derived from selected lanolins, modified by reaction with ethylene oxide to give it water solubility. PEG-75 is commercially available as Laneto-50 from Rita Corporation of Crystal Lake, Il.

When a conditioner is to be utilized, it is mixed into the aqueous calcium chloride solution prior to impregnating the end wrap paper sheet. Although the effect of the conditioner increases with its concentration, too high of a concentration can interfere with the neutralizing effects of the calcium chloride. It has been found that the conditioner should not exceed about 50% of the solution, by volume, with about 25%, by volume, of conditioner being preferred. The procedure for impregnating the end wrap paper sheet with a solution with a conditioner additive is the same as discussed above.

In use, the end wrap laminates of the present invention are applied to the ends or desired locations of hair tressels in a conventional manner with the section of hair sandwiched between and contacting the interior sheet of impregnated paper. After the rolling operation is complete, the permanent hair treatment proceeds in a conventional manner. Once all of the hair waving steps are complete, the rollers and end wraps are removed, and a final water rinse is administered to insure complete removal of any residual calcium chloride and neutralization reaction products.

The following examples further illustrate the treated end wrap laminates of the present invention:

EXAMPLE I

A one foot by one foot sheet of textured polyethylene having a thickness of 0.3 mils is placed on a table. A thin coating of 3M Spray Adhesive 90 is then sprayed uniformly on the surface of the polyethylene sheet. A one foot by one foot sheet of wet strength tissue paper having a density of nine pounds per cubic foot and a thickness of 1.5 mils is then placed on the adhesive covered polyethylene sheet. The laminate is permitted to dry for five minutes.

Fifty grams of calcium chloride crystals are added to a mixing vessel. Water is then added to the vessel with mixing until the calcium chloride is completely dissolved. The calcium chloride solution is then uniformly brushed onto the paper sheet of the end wrap laminate until it is thoroughly saturated. The laminate is permitted to dry for four hours to substantially evaporate the water. The laminate is then cut into 24 2-inch by 3-inch end wraps.

An individual's hair is washed and separated into tresses. An end wrap laminate is folded over each wet hair tress end so that all of the free ends are covered. Each wrapped tress is wound upon a curler and secured. A commercially available hair waving solution, Moisture Wave, produced by Zotos International of Darian, Connecticut, the active ingredient of which is ammonium thioglycolate, is applied to the wound tresses. After waiting fifteen minutes, the wound tresses are rinsed with water and blotted. The head is then covered with a towel, and after an additional thirty minutes, the hair is neutralized with a 3% hydrogen peroxide solution. The curlers and the end papers are then removed from the hair, and then the hair is again thoroughly rinsed with water. The hair is then set in a normal fashion and dried. The tress ends which were covered by the end wraps show no evidence of any curl or wave, whereas the uncovered portions of the hair have an excellent uniform wave.

EXAMPLE II

The procedures of Example I are repeated, except that LANITO 50 (PEG-75 lanolin) is added to the calcium chloride solution prior to impregnating the end wrap paper sheet. An amount of LANITO 50 equal to 1/3 the volume of the aqueous calcium chloride solution is added. Upon completion of the hair treatment, inspection of the tressel ends which were covered by the end wrap with the conditioner additive revealed an increased sheen and lustre as compared to the tressel ends of Example I.

Thus, the unique treated end wrap laminates of the present invention are inexpensive and easy to fabricate and provide a dual protection for hair ends from hair waving solution. The invention also provides the surprising discovery of the use of calcium chloride as a waving solution counteractant.

While the preferred embodiments of the present invention have been described and illustrated, it will be obvious to those skilled in the art that various changes and modifications can be made without departing from the spirit of the present invention. Accordingly, the scope of the present invention is deemed to be limited only by the appended claims.

The embodiments of the invention in which an exclusive property or privilege is claimed are defined as follows:

1. A treated end wrap laminate for use in permanent hair waving comprising
   an exterior sheet of impermeable flexible plastic;
   an interior sheet of absorbent flexible paper impregnated with a hair waving solution counteractant and having a configuration corresponding to said exterior sheet; and
   a middle layer of adhesive uniformly bonding said sheets together.

2. A treated end wrap laminate according to claim 1 wherein said plastic is polyethylene and said paper is tissue paper.

3. A treated end wrap laminate according to claim 2 wherein the configuration of said sheets is rectangular, said plastic has a thickness of from about 0.2 to about 1.0 mils, and said paper has a thickness of from about 1 to about 2 mils.

4. A treated end wrap laminate according to claim 3 wherein said paper is wet strength tissue paper having a density of from about 8 to about 10 pounds per cubic foot.

5. A treated end wrap laminate according to claim 4 wherein said polyethylene is texturized.

6. A treated end wrap laminate according to claim 1 wherein said paper is impregnated with said calcium chloride by applying an aqueous solution of calcium chloride to said paper followed by evaporating substantially all of the water.

7. A treated end wrap laminate according to claim 6 wherein said aqueous solution of calcium chloride is a substantially saturated solution.

8. A treated end wrap laminate according to claim 1 wherein said paper is also impregnated with at least one hair conditioner.

9. A treated end wrap laminate according to claim 1 wherein said plastic is polyethylene and said paper is tissue paper.

10. A treated end wrap laminate according to claim 9 wherein the configuration of said sheets is rectangular, said plastic has a thickness of from about 0.2 to about 1.0 mils, and said paper has a thickness of from about 1 to about 2 mils.

11. A treated end wrap laminate according to claim 19 wherein said paper is wet strength tissue paper having a density of from about 8 to about 10 pounds per cubic foot.

12. A treated end wrap laminate according to claim 11 wherein said polyethylene is texturized.

13. A hair waving solution counteractant comprising calcium chloride.

14. A hair waving solution counteractant according to claim 13 wherein the active ingredient of said hair waving solution is a thioglycolic compound.

15. An end wrap laminate for treating hair comprising a sheet of impermeable flexible plastic bonded to a mating sheet of an absorbent, flexible wet strength tissue paper, with the paper being impregnated with calcium chloride.

16. An end wrap laminate according to claim 15 wherein the tissue paper also is impregnated with a hair conditioner that retards any increased rate of drying caused by the calcium chloride.

17. An end wrap laminate according to claim 15 wherein the plastic is a layer of polyehtylene about 0.2 to 1.0 mils thick.

18. An end wrap lamiante according to claim 15 wherein the paper and plastic are bonded together with an intermediate adhesive layer that is water resistant and non-reactive to hair waving chemicals.

19. A treated end wrap laminate for use in permanent hair waving with a hair waving solution, wherein the active ingredient is a thioglycolic compound, comprising:

an exterior sheet of impermeable flexible plastic;

an interior sheet of absorbent flexible paper having a configuration corresponding to said exterior sheet, the paper being impregentated with a hair waving solution counteractant comprising calcium chloride; and a middle layer of adhesive uniformly bonding said sheets together.

* * * * *

UNITED STATES PATENT AND TRADEMARK OFFICE
CERTIFICATE OF CORRECTION

PATENT NO. : 4,632,132

DATED : 12-30-86

INVENTOR(S) : William G. Bustance; Robert E. Borey

It is certified that error appears in the above-identified patent and that said Letters Patent are hereby corrected as shown below:

Column 6, Line 32, delete the numeral "1" and substitute the numeral -- 19 --.

Column 6, Line 40, delete the numeral "1" and substitute the numeral -- 19 --.

Column 6, Line 43, delete the numeral "1" and substitute the numeral -- 19 --.

Column 6, Line 52, delete the numeral "19" and substitute the numeral -- 10 --.

Column 7, Line 4, delete "polyehtylene" and substitute -- polyethylene --.

Signed and Sealed this

Fifteenth Day of September, 1987

Attest:

DONALD J. QUIGG

*Attesting Officer*    *Commissioner of Patents and Trademarks*